United States Patent
Cohen-Tzemach et al.

(10) Patent No.: US 10,179,043 B2
(45) Date of Patent: Jan. 15, 2019

(54) PROSTHETIC HEART VALVE HAVING MULTI-LEVEL SEALING MEMBER

(71) Applicant: Edwards Lifesciences Corporation, Irvine, CA (US)

(72) Inventors: Hanoch Cohen-Tzemach, Holon (IL); Tamir S. Levi, Moshav Ein HaEmek (IL); Noam Nir, Gesher Haziv (IL); Bella Felsen, Haifa (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/425,029

(22) Filed: Feb. 6, 2017

(65) Prior Publication Data
US 2017/0231761 A1     Aug. 17, 2017

Related U.S. Application Data

(60) Provisional application No. 62/294,739, filed on Feb. 12, 2016.

(51) Int. Cl.
*A61F 2/24* (2006.01)
(52) U.S. Cl.
CPC .... *A61F 2/2418* (2013.01); *A61F 2210/0014* (2013.01); *A61F 2220/0075* (2013.01);
(Continued)
(58) Field of Classification Search
CPC ......... A61F 2/24; A61F 2/2412; A61F 2/2418
(Continued)

(56) References Cited

U.S. PATENT DOCUMENTS 3,365,728 A   1/1968   Edwards et al.
3,409,013 A   11/1968  Berry
(Continued)

FOREIGN PATENT DOCUMENTS

AU    2002212418 B2   3/2006
DE       2246526 A1   3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Suzette J Gherbi
(74) *Attorney, Agent, or Firm* — Joel B. German; AnneMarie Kaiser; Klarquist Sparkman LLC (57) ABSTRACT

Embodiments of a prosthetic heart valve are disclosed. An implantable prosthetic valve may be radially collapsible to a collapsed configuration and radially expandable to an expanded configuration. The prosthetic valve may comprise an annular frame, a leaflet structure positioned within the frame and a plurality of outer skirts positioned around an outer surface of the frame, each outer skirt comprising an inflow edge secured to the frame and an outflow edge secured at intervals to the frame. The plurality of outer skirts may include a first outer skirt and a second outer skirt, wherein in the expanded configuration the first and second outer skirts include openings unsecured to the frame between the intervals. The inflow edge of the first annular outer skirt may be secured to the frame with sutures including radiopaque material. The first annular outer skirt may include radiopaque dye.

19 Claims, 7 Drawing Sheets

(52) U.S. Cl.
CPC .............. *A61F 2230/0017* (2013.01); *A61F 2230/0026* (2013.01); *A61F 2230/0069* (2013.01); *A61F 2250/0069* (2013.01); *A61F 2250/0098* (2013.01)

(58) Field of Classification Search
USPC .................................................. 623/2.1–2.19
See application file for complete search history.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,983,581 A | 10/1976 | Angell et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,258,023 A | 11/1993 | Reger |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,383,925 A * | 1/1995 | Schmitt ............... A61F 2/06 600/36 |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,476,506 A | 12/1995 | Lunn |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,786 A | 5/1997 | Banas et al. |
| 5,628,792 A | 5/1997 | Lentell |
| 5,639,274 A | 6/1997 | Fischell et al. |
| 5,665,115 A | 9/1997 | Cragg |
| 5,693,088 A | 12/1997 | Lazarus |
| 5,716,417 A | 2/1998 | Girard et al. |
| 5,728,068 A | 3/1998 | Leone et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,776,188 A | 7/1998 | Shepherd et al. |
| 5,800,508 A | 9/1998 | Goicoechea et al. |
| 5,840,081 A | 11/1998 | Andersen et al. |
| 5,843,161 A | 12/1998 | Solovay |
| 5,843,179 A | 12/1998 | Vanney et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,015,431 A | 1/2000 | Thornton et al. |
| 6,027,525 A | 2/2000 | Suh et al. |
| 6,110,198 A | 8/2000 | Fogarty et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,206,911 B1 | 3/2001 | Milo |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,350,277 B1 | 2/2002 | Kocur |
| 6,352,547 B1 | 3/2002 | Brown et al. |
| 6,352,554 B2 | 3/2002 | De Paulis |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,540,782 B1 | 4/2003 | Snyders |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |

(56) References Cited

U.S. PATENT DOCUMENTS

| | | |
|---|---|---|
| 6,663,667 B2 | 12/2003 | Dehdashtian et al. |
| 6,689,123 B2 | 2/2004 | Pinchasik |
| 6,716,244 B2 | 4/2004 | Klaco |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,773,456 B1 | 8/2004 | Gordon et al. |
| 6,783,542 B2 | 8/2004 | Eidenschink |
| 6,814,754 B2 | 11/2004 | Greenhalgh |
| 6,830,584 B1 | 12/2004 | Seguin |
| 6,846,325 B2 | 1/2005 | Liddicoat |
| 6,878,162 B2 | 4/2005 | Bales et al. |
| 6,893,460 B2 | 5/2005 | Spenser et al. |
| 6,904,909 B2 | 6/2005 | Andreas et al. |
| 6,908,481 B2 | 6/2005 | Cribier |
| 6,911,040 B2 | 6/2005 | Johnson et al. |
| 6,936,067 B2 | 8/2005 | Buchanan |
| 6,951,573 B1 * | 10/2005 | Dilling .................. A61F 2/2403 623/2.1 |
| 7,018,406 B2 | 3/2006 | Seguin et al. |
| 7,018,408 B2 | 3/2006 | Bailey et al. |
| 7,096,554 B2 | 8/2006 | Austin et al. |
| 7,101,396 B2 | 9/2006 | Artof et al. |
| 7,147,663 B1 | 12/2006 | Berg et al. |
| 7,175,652 B2 | 2/2007 | Cook et al. |
| 7,192,441 B2 | 3/2007 | Sherry |
| 7,225,518 B2 | 6/2007 | Eidenschink et al. |
| 7,264,632 B2 | 9/2007 | Wright et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,731,742 B2 | 6/2010 | Schlick et al. |
| 7,780,725 B2 | 8/2010 | Haug et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,105,377 B2 | 1/2012 | Liddicoat |
| 8,128,681 B2 | 3/2012 | Shoemaker et al. |
| 8,167,932 B2 | 5/2012 | Bourang et al. |
| 8,291,570 B2 | 10/2012 | Eidenschink et al. |
| 8,425,593 B2 | 4/2013 | Braido et al. |
| 8,430,925 B2 | 4/2013 | Forster et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,721,717 B2 | 5/2014 | Shoemaker et al. |
| 8,747,463 B2 | 6/2014 | Fogarty et al. |
| 8,795,357 B2 | 8/2014 | Yohanan et al. |
| 8,808,356 B2 | 8/2014 | Braido et al. |
| 8,845,721 B2 | 9/2014 | Braido et al. |
| 8,979,922 B2 | 3/2015 | Jayasinghe et al. |
| 8,992,608 B2 | 3/2015 | Haug et al. |
| 9,078,781 B2 | 7/2015 | Ryan et al. |
| 9,220,594 B2 | 12/2015 | Braido et al. |
| 9,241,794 B2 | 1/2016 | Braido et al. |
| 9,289,296 B2 | 3/2016 | Braido et al. |
| 9,326,856 B2 | 5/2016 | Schraut et al. |
| 9,345,571 B1 | 5/2016 | Braido et al. |
| 9,351,828 B2 | 5/2016 | Braido et al. |
| 9,351,831 B2 | 5/2016 | Braido et al. |
| 9,351,832 B2 | 5/2016 | Braido et al. |
| 9,414,911 B2 | 8/2016 | Braido et al. |
| 9,545,307 B2 | 1/2017 | Braido et al. |
| 9,549,815 B2 | 1/2017 | Braido et al. |
| 2001/0021872 A1 | 9/2001 | Bailey et al. |
| 2001/0027338 A1 | 10/2001 | Greenberg |
| 2001/0039450 A1 | 11/2001 | Pavcnik et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0173842 A1 | 11/2002 | Buchanan |
| 2003/0050694 A1 | 3/2003 | Yang et al. |
| 2003/0074058 A1 | 4/2003 | Sherry |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2003/0236567 A1 | 12/2003 | Elliot |
| 2004/0033364 A1 | 2/2004 | Spiridigliozzi et al. |
| 2004/0039436 A1 | 2/2004 | Spenser et al. |
| 2004/0082989 A1 | 4/2004 | Cook et al. |
| 2004/0098096 A1 | 5/2004 | Eton |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0043790 A1 | 2/2005 | Seguin |
| 2005/0075728 A1 | 4/2005 | Nguyen et al. |
| 2005/0096736 A1 | 5/2005 | Osse et al. |
| 2005/0137687 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2006/0183383 A1 | 8/2006 | Asmus et al. |
| 2006/0195184 A1 * | 8/2006 | Lane ..................... A61F 2/2409 623/2.38 |
| 2006/0229719 A1 | 10/2006 | Marquez et al. |
| 2006/0259137 A1 | 11/2006 | Artof et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0073387 A1 | 3/2007 | Forster et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0082161 A1 * | 4/2008 | Woo ..................... A61F 2/0095 623/1.26 |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0275537 A1 | 11/2008 | Limon |
| 2009/0099653 A1 | 4/2009 | Suri et al. |
| 2009/0125118 A1 | 5/2009 | Gong |
| 2009/0132035 A1 | 5/2009 | Roth et al. |
| 2009/0157175 A1 | 6/2009 | Benichou |
| 2009/0192591 A1 | 7/2009 | Ryan et al. |
| 2009/0276040 A1 | 11/2009 | Rowe et al. |
| 2009/0281619 A1 | 11/2009 | Le et al. |
| 2009/0299452 A1 | 12/2009 | Eidenschink et al. |
| 2009/0319037 A1 | 12/2009 | Rowe et al. |
| 2010/0049313 A1 | 2/2010 | Alon et al. |
| 2010/0168839 A1 | 7/2010 | Braido et al. |
| 2010/0168844 A1 | 7/2010 | Toomes et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0319991 A1 | 12/2011 | Hariton et al. |
| 2012/0035719 A1 | 2/2012 | Forster et al. |
| 2012/0123529 A1 | 5/2012 | Levi et al. |
| 2012/0215303 A1 | 8/2012 | Quadri et al. |
| 2012/0259409 A1 | 10/2012 | Nguyen et al. |

(56) References Cited

U.S. PATENT DOCUMENTS

| | | | |
|---|---|---|---|
| 2013/0023985 A1 | 1/2013 | Khairkhahan et al. | |
| 2013/0190857 A1 | 7/2013 | Mitra et al. | |
| 2013/0190862 A1* | 7/2013 | Pintor | A61F 2/2403 623/2.18 |
| 2013/0274873 A1 | 10/2013 | Delaloye et al. | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2013/0338765 A1 | 12/2013 | Braido et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0277389 A1* | 9/2014 | Braido | A61F 2/2418 623/1.26 |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0330372 A1 | 11/2014 | Weston et al. | |
| 2014/0343671 A1 | 11/2014 | Yohanan et al. | |
| 2014/0350663 A1 | 11/2014 | Braido et al. | |
| 2014/0350667 A1 | 11/2014 | Braido et al. | |
| 2015/0073541 A1 | 3/2015 | Salahieh et al. | |
| 2015/0073545 A1 | 3/2015 | Braido | |
| 2015/0073546 A1 | 3/2015 | Braido | |
| 2015/0157455 A1* | 6/2015 | Hoang | A61F 2/2418 623/2.18 |
| 2015/0282932 A1 | 10/2015 | Neuman et al. | |
| 2015/0313711 A1* | 11/2015 | Chang | A61F 2/2427 623/2.11 |
| 2015/0327996 A1* | 11/2015 | Fahim | A61F 2/2418 623/2.17 |
| 2016/0213466 A1 | 7/2016 | Braido et al. | |
| 2016/0213468 A1 | 7/2016 | Braido et al. | |
| 2016/0242904 A1* | 8/2016 | Braido | A61F 2/2412 |
| 2016/0310267 A1* | 10/2016 | Zeng | A61F 2/2418 |
| 2016/0317305 A1* | 11/2016 | Pelled | B29C 66/53245 |
| 2016/0346105 A1* | 12/2016 | Lee | A61F 2/91 |
| 2016/0374802 A1* | 12/2016 | Levi | A61F 2/2412 623/2.14 |
| 2017/0135812 A1* | 5/2017 | Park | A61B 17/04 |
| 2017/0172736 A1* | 6/2017 | Chadha | A61F 2/24 |
| 2017/0218228 A1* | 8/2017 | Jose | C09D 11/03 |
| 2018/0008402 A1* | 1/2018 | Braido | A61F 2/2412 |
| 2018/0021129 A1* | 1/2018 | Peterson | A61F 2/2409 623/2.17 |
| 2018/0021131 A1* | 1/2018 | Zeng | A61F 2/2418 623/2.17 |
| 2018/0036122 A1* | 2/2018 | Bergheim | A61F 2/2409 |

FOREIGN PATENT DOCUMENTS

| | | |
|---|---|---|
| DE | 0144167 C | 6/1985 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1570809 A1 | 9/2005 |
| EP | 1796597 A2 | 6/2007 |
| EP | 2155114 A1 | 2/2010 |
| EP | 2299938 A2 | 3/2011 |
| EP | 2572675 A2 | 3/2013 |
| EP | 2572676 A2 | 3/2013 |
| EP | 2698129 A1 | 2/2014 |
| EP | 2745805 A1 | 6/2014 |
| EP | 2749254 A1 | 7/2014 |
| EP | 2815723 A1 | 12/2014 |
| EP | 2815724 A1 | 12/2014 |
| EP | 2815725 A1 | 12/2014 |
| EP | 2967851 A2 | 1/2016 |
| EP | 2926766 B1 | 2/2016 |
| EP | 3028670 A1 | 6/2016 |
| EP | 3028671 A1 | 6/2016 |
| EP | 3025680 B1 | 2/2017 |
| EP | 3025681 B1 | 2/2017 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9748350 A8 | 6/1999 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0044313 A1 | 8/2000 |
| WO | 0047139 A1 | 8/2000 |
| WO | 0106959 A1 | 2/2001 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0219951 A1 | 3/2002 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03003949 A2 | 1/2003 |
| WO | 03047468 A1 | 6/2003 |
| WO | 03037222 A3 | 10/2003 |
| WO | 03088873 A1 | 10/2003 |
| WO | 03096932 A1 | 11/2003 |
| WO | 2005034812 | 4/2005 |
| WO | 2005084595 A1 | 9/2005 |
| WO | 2006014233 A2 | 2/2006 |
| WO | 2006034008 A2 | 3/2006 |
| WO | 2006005015 A3 | 4/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009042196 A2 | 4/2009 |
| WO | 2010121076 A2 | 10/2010 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

(56) References Cited

OTHER PUBLICATIONS

Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.

\* cited by examiner

PROSTHETIC HEART VALVE HAVING MULTI-LEVEL SEALING MEMBER

CROSS REFERENCE TO RELATED APPLICATION

This application claims the benefit of U.S. Provisional Patent Application No. 62/294,739, filed Feb. 12, 2016, which is incorporated herein by reference.

FIELD

The present disclosure concerns embodiments of a prosthetic heart valve.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans.

Various surgical techniques may be used to replace or repair a diseased or damaged valve. Due to stenosis and other heart valve diseases, thousands of patients undergo surgery each year wherein the defective native heart valve is replaced by a prosthetic valve. Another less drastic method for treating defective valves is through repair or reconstruction, which is typically used on minimally calcified valves. The problem with surgical therapy is the significant risk it imposes on these chronically ill patients with high morbidity and mortality rates associated with surgical repair.

When the native valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective native valves are deemed inoperable because their condition is too frail to withstand the procedure. By some estimates, more than 50% of the subjects suffering from valve stenosis who are older than 80 years cannot be operated on for valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. Nos. 5,411,522 and 6,730,118, which are incorporated herein by reference, describe collapsible transcatheter heart valves that can be percutaneously introduced in a compressed state on a catheter and expanded in the desired position by balloon inflation or by utilization of a self-expanding frame or stent.

An important design parameter of a transcatheter heart valve is proper positioning of the heart valve, for example on the balloon prior to inflation as well as at implantation location, so as to prevent final positioning of a reversed valve. A further important design parameter is minimization of paravalvular leak (PVL). PVL may include complications such as blood flowing through a channel between the structure of the implanted valve and cardiac tissue, for example as a result of a lack of appropriate sealing.

SUMMARY

An exemplary embodiment of a prosthetic heart valve may include an annular frame, a leaflet structure positioned within the frame, and two or more annular outer skirts positioned around an outer surface of the frame. The two or more outer skirts may each comprise an inflow edge secured to the frame and an outflow edge, wherein the outflow edges of the two or more outer skirts may define one or more upper openings allowing retrograde blood flow between the outer surface of the frame and the two or more skirts to create a plurality of regions of turbulent blood flow along the prosthetic valve.

Some embodiments of an implantable prosthetic valve may be radially collapsible to a collapsed configuration and radially expandable to an expanded configuration. Some embodiments of the prosthetic valve may comprise an annular frame, a leaflet structure positioned within the frame, and a plurality of outer skirts positioned around an outer surface of the frame. Each outer skirt may comprise an inflow edge secured to the frame and an outflow edge secured at intervals to the frame. The plurality of outer skirts may include a first outer skirt and a second outer skirt, wherein in the expanded configuration the first and the second outer skirts may include openings unsecured to the frame between the intervals.

In some embodiments, the inflow edge of the first outer skirt may be secured to the frame with sutures including radiopaque material. In some embodiments, the first outer skirt may comprise markings formed from radiopaque dye.

In some embodiments, the openings of the first outer skirt and the second outer skirt may be circumferentially aligned. Additionally and/or alternatively, in some embodiments, the openings may not lie flat against the outer surface of the frame and are spaced radially outward from the frame in the expanded configuration. Additionally and/or alternatively, the inflow edge of the second outer skirt may contact the outflow edge of the first outer skirt without any axial spacing between. The outflow edge of at least one of the plurality of outer skirts may be unsecured to the frame. The plurality of outer skirts may be positioned in series along the length of the frame between an inflow edge of the frame and an outflow edge of the frame. The axial height of a least two of the plurality of skirts may be the same.

Some embodiments of a prosthetic heart valve may include an annular frame having an inflow end and an outflow end, a leaflet structure positioned within the frame and an annular skirt mounted on the frame. The skirt may comprise radiopaque markings, which can comprise one or both of radiopaque sutures and radiopaque dye, to facilitate positioning of the prosthetic valve under fluoroscopy.

The foregoing and other objects, features, and advantages of the disclosure will become more apparent from the following detailed description, which proceeds with reference to the accompanying figures.

DETAILED DESCRIPTION

For purposes of this description, certain aspects, advantages, and novel features of the embodiments of this disclosure are described herein. Features, integers, characteristics, compounds, chemical moieties or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

Figure 1:
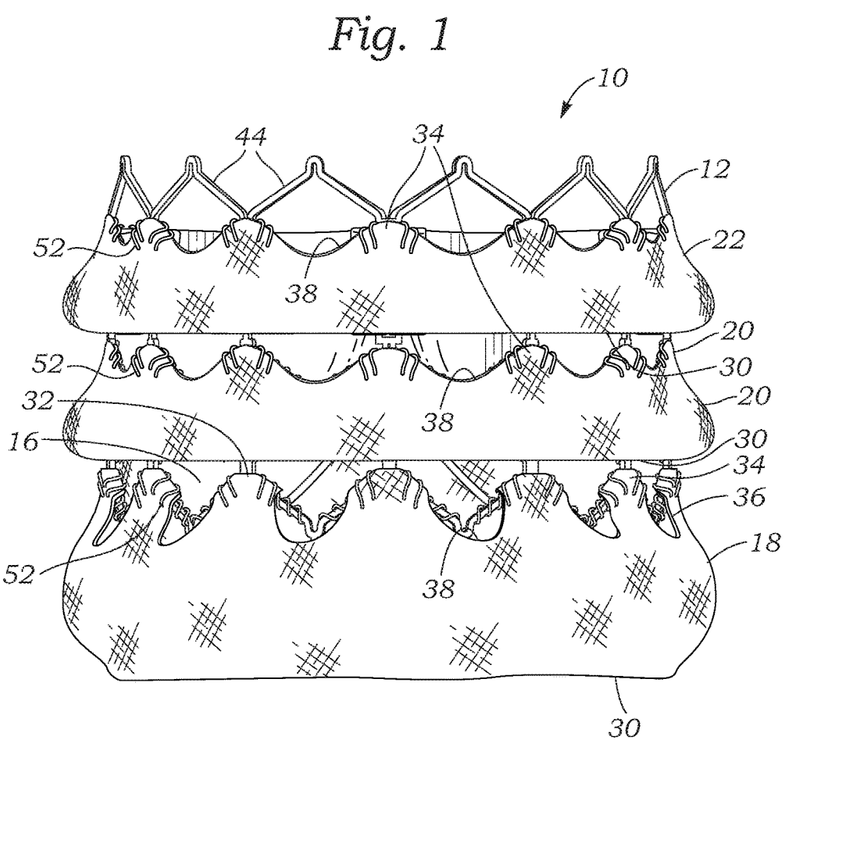
FIG. 1 shows a perspective view an exemplary embodiment of a prosthetic heart valve.
Figure 2:
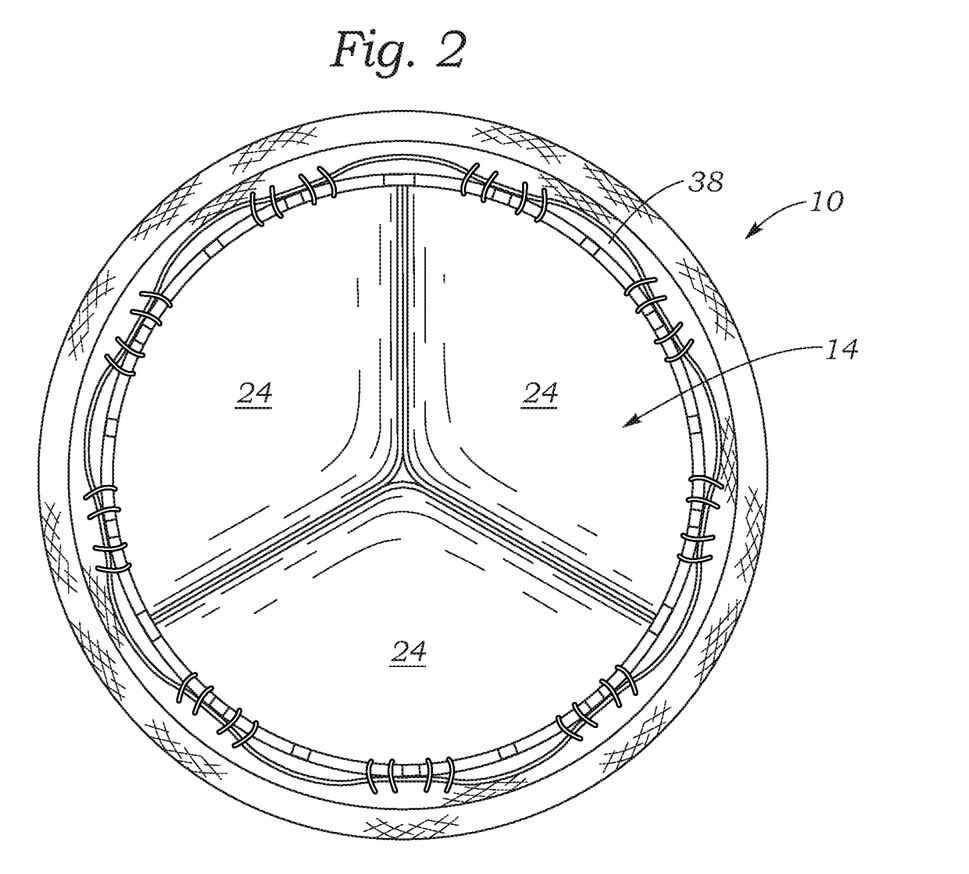
FIG. 2 shows a top view of the prosthetic heart valve of FIG. 1

FIGS. 1 and 2 show perspective and top plan views, respectively, of a prosthetic heart valve 10, according to one embodiment. The illustrated prosthetic valve is adapted to be implanted in the native aortic annulus, although in other embodiments it can be adapted to be implanted in the other native annuluses of the heart (the mitral valve, pulmonary valve and triscupid valve). The prosthetic valve 10 may have one or more of the following components: a stent, or frame, 12, a valvular structure 14 and/or an inner skirt, or sealing member, 16. The valve 10 may also include two or more outer skirts, or sealing members. For example, the valve may include a first outer skirt, or sealing member, 18, a second outer skirt, or sealing member, 20 and a third outer skirt, or sealing member, 22.

The valvular structure 14 can comprise three leaflets 24, collectively forming a leaflet structure, which can be arranged to collapse in a tricuspid arrangement, as best shown in FIG. 2. The lower edge of leaflet structure 14 desirably has an undulating, curved scalloped shape. By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve. The leaflets 24 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein. Further details regarding the structure of the leaflets and the technique for mounting the leaflets 24 to the frame and the inner skirt are disclosed in U.S. Publication No. 2012/0123529, which is incorporated herein by reference.

Figure 3:
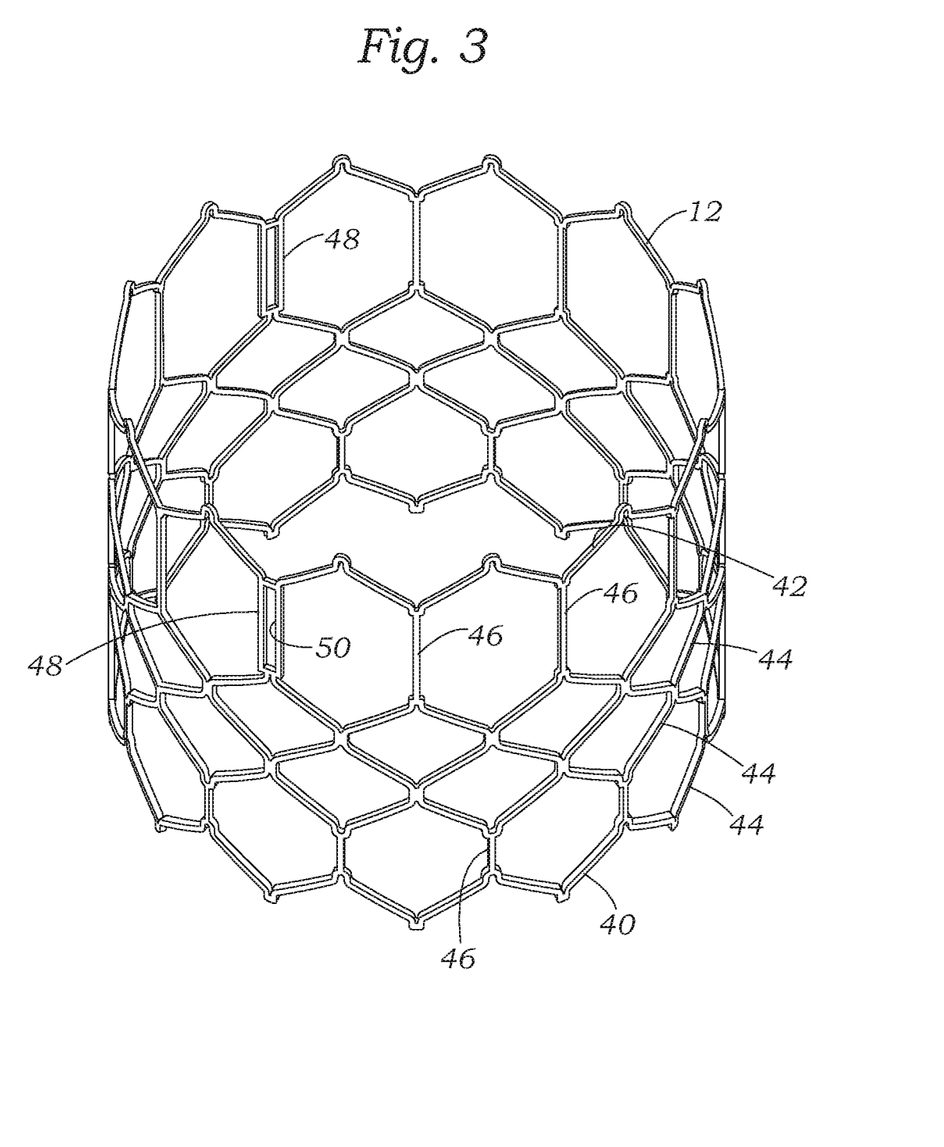
FIG. 3 shows a perspective view of an exemplary frame of the prosthetic heart valve of FIG. 1.

The bare frame 12 is shown in FIG. 3. The frame 12 has an inflow end 40 and an outflow end 42. The frame 12 in the illustrated embodiment comprises a plurality of angled struts 44 arranged in a plurality of circumferential rows of struts along the length of the frame. One or more pairs of adjacent rows of angled struts 44 can be connected by vertical struts 46. The rows of struts 44 closet to the outflow end of frame 12 also can be connected to each other with a plurality of circumferentially spaced commissure supports 48 (for example, three) and vertical struts 46. The commissure supports 48 can be formed with respective slots, or commissure windows, 50 that are adapted to mount the commissures of the valvular structure 14 to the frame, as described in greater detail below.

The frame 12 can be made of any of various suitable plastically-expandable materials (e.g., stainless steel, etc.) or self-expanding materials (e.g., Nitinol) as known in the art. Alternatively, the frame can be mechanically-expandable. When constructed of a plastically-expandable material, the frame 12 (and thus the prosthetic valve 10) can be crimped to a radially compressed state on a delivery catheter and then expanded inside a patient by an inflatable balloon or equivalent expansion mechanism. When constructed of a self-expandable material, the frame 12 (and thus the prosthetic valve 10) can be crimped to a radially compressed state and restrained in the compressed state by insertion into a sheath or equivalent mechanism of a delivery catheter. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 provides superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

The frame 12 can have other configurations or shapes in other embodiments. For example, the frame 12 can comprise a plurality of circumferential rows of angled struts 44 connected directly to each other without vertical struts 46 or commissure supports 48 between adjacent rows of struts 44, or the rows of struts 44 can be evenly spaced with vertical struts 46 and/or commissure supports 48. In other embodiments, the frame can comprise a braided metal.

The inner skirt 16 may have a plurality of functions, which may include to assist in securing the valvular structure 14 and/or the outer skirts to the frame 12 and to assist in forming a good seal between the valve and the native annulus by blocking the flow of blood through the open cells of the frame 12 below the lower edge of the leaflets. The inner skirt 16 may comprise a tough, tear resistant material such as polyethylene terephthalate (PET), although various other synthetic or natural materials can be used. The thickness of the skirt desirably is less than 6 mil, and desirably less than 4 mil, and even more desirably about 2 mil. In particular embodiments, the skirt 16 can have a variable thickness, for example, the skirt can be thicker at its edges than at its center. In one implementation, the skirt 16 can comprise a PET skirt having a thickness of about 0.07 mm at its edges and about 0.06 mm at its center. The thinner skirt can provide for better crimping performances while still providing good perivalvular sealing.

Figure 4:
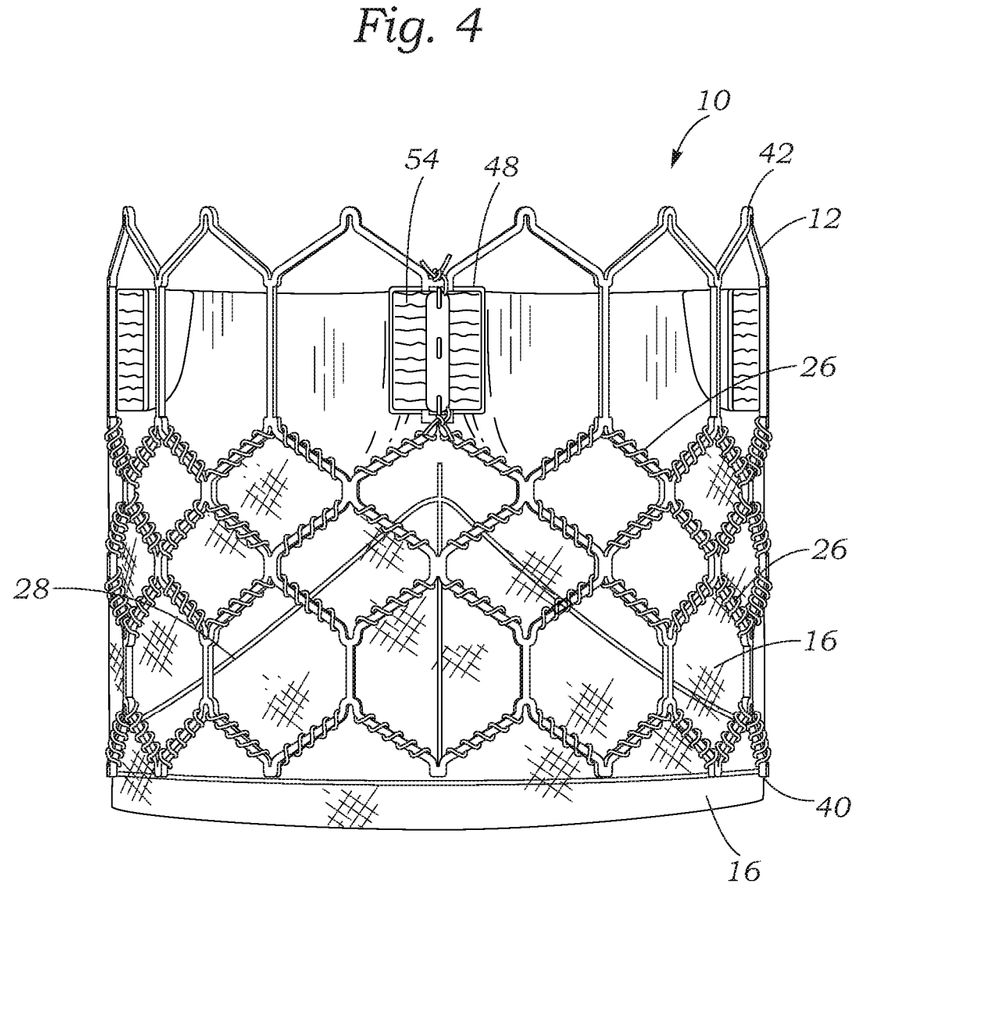
FIG. 4 shows a side elevation view of the prosthetic heart valve of FIG. 1 with the outer skirts removed to show the assembly of an inner skirt and valvular structure mounted on the frame.

FIG. 4 shows the frame 12, leaflet structure 14 and the inner skirt 16 after securing the leaflet structure to the inner skirt to the frame and then securing these components to the frame. The inner skirt 16 can be secured to the inside of frame 12 via sutures 26. Valvular structure 14 can be attached to the inner skirt via one or more thin PET reinforcing strips (not shown) along the lower (inflow) edges of the leaflets. The reinforcing strips collectively can form a sleeve, which may enable a secure suturing and protect the pericardial tissue of the leaflet structure from tears. Valvular structure 14 can be sandwiched between the inner skirt 16 and the thin PET strips. Sutures 28, which secure the PET strips and the leaflet structure 14 to inner skirt 16, can be any suitable suture, such as an Ethibond suture. Sutures 28 desirably track the curvature of the bottom edge of leaflet structure 14. The outflow end portion of the valvular structure 14 can be secured to the commissure supports 48. In particular, each leaflet 24 can have opposing tab portions, each of which is paired with an adjacent tab portion of another leaflet to form a commissure 54. As best shown in FIG. 4, the commissures 54 can extend through windows 50 of respective commissure supports 48 and sutured in place.

In FIG. 4, the inner skirt 16 terminates short of the commissures supports 48 and does not extend the entire length of the frame 12. In alternative embodiments, the inner skirt 16 can extend the entire length or substantially the entire length of the frame 12 from the inflow end 40 to the outflow end 42. Extending the inner skirt 16 the entire length of the frame 12 can be advantageous for use in securing the outer skirts to the frame at any location along the length of the frame.

Known fabric skirts comprise a weave of warp and weft fibers that extend perpendicular to each other and with one set of fibers extending perpendicularly to the upper and lower edges of the skirt. When the metal frame, to which the fabric skirt is secured, is radially compressed, the overall axial length of the frame increases. Unfortunately, a fabric skirt, which inherently has limited elasticity, cannot elongate along with the frame and therefore tends to deform the struts of the frame and prevents uniform crimping.

The inner skirt may be woven from a first set of fibers, or yarns or strands, and a second set of fibers, or yarns or strands, both of which are non-perpendicular to the upper edge and the lower edge of the skirt. In particular embodiments, the first set of fibers and the second set of fibers extend at angles of about 45 degrees relative to the upper and lower edges. The inner skirt 16 can be formed by weaving the fibers at 45 degree angles relative to the upper and lower edges of the fabric. Alternatively, the skirt can be diagonally cut from a vertically woven fabric (where the fibers extend perpendicular to the edges of the material) such that the fibers extend at 45 degree angles relative to the cut upper and lower edges of the skirt. The opposing short edges of the inner skirt desirably are non-perpendicular to the upper and lower edges. For example, the short edges desirably extend at angles of about 45 degrees relative to the upper and lower edges and therefore are aligned with the first set of fibers. Therefore the overall shape of the inner skirt may be that of a rhomboid.

As shown in FIG. 1, the valve 10 may include two or more outer skirts mounted on the outside of the frame 12. The two or more outer skirts may be assembled on the valve 10 outer diameter and may be positioned at different levels or locations along the length of the frame. For example, as shown in FIG. 1, the valve 10 may include the first outer skirt 18, the second outer skirt 20 and the third outer skirt 22. One or more of the first, second and third outer skirts 18, 20, 22 may be sutured to the inner skirt. Additionally and/or alternatively, one or more of the first, second and third outer skirts 18, 20, 22 may be sutured to the frame. Each outer skirt desirably comprises a tubular or cylindrical shape when mounted on the frame 12 so as to extend completely around the outer surface of the frame.

Figure 5:
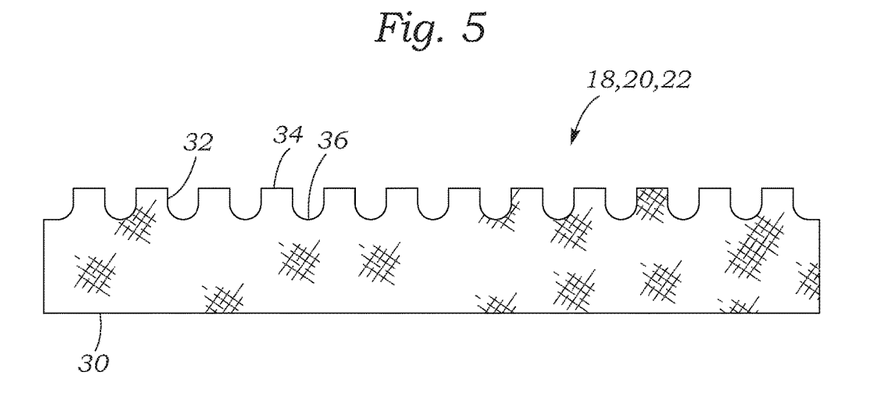
FIG. 5 shows an exemplary outer skirt laid out flat.

FIG. 5 shows a flattened view of one of the outer skirts 18, 20, 22 prior to its attachment to the frame 12 and/or inner skirt 16. The outer skirts 18, 20, 22 can be laser cut or otherwise formed from a strong, durable piece of material, such as woven PET, although other synthetic or natural materials can be used. The outer skirts 18, 20, 22 can have a substantially straight lower edge 30 and an upper edge 32 defining a plurality of alternating projections 34 and notches 36. While the illustrated embodiment includes three such outer skirts, the prosthetic valve can have two outer skirts or more than three outer skirts (e.g., four, five, or six outer skirts) in alternative embodiments. Each outer skirt 18, 20, 22 can have the same height (measured from the lower edge 30 to the upper edge). In alternative embodiments, the height of the outer skirts can vary from one outer skirt to the next.

As best shown in FIG. 1, the lower edge 30 of the first outer skirt 18 can be sutured to the lower edge of the inner skirt 16 and/or the first rung of struts 44 of the frame at the inflow end of the prosthetic valve. The lower edge 30 of the second outer skirt 20 can be sutured to the inner skirt 16 and/or the struts 44 of the frame 12 downstream and adjacent the upper edge 32 of the first outer skirt 18. The lower edge 30 of the third outer skirt 22 can be sutured to the inner skirt 16 and/or the struts 44 of the frame 12 downstream and adjacent the upper edge 32 of the second outer skirt 20. In particular embodiments, the lower edges 30 of the outer skirt 18, 20, 22 are tightly sutured or otherwise secured (e.g., by welding or an adhesive) to the inner skirt 16 to catch retrograde blood flowing between the frame and the outer skirts, as further described below.

The outer skirts 18, 20, 22 can be slightly axially spaced from each other along the length of the frame 12 so that there is some spacing between the lower edge of one outer skirt and the upper edge of an adjacent outer skirt. In alternative embodiment, the outer skirts 18, 20, 22 can be positioned relative to each other with the lower edge 30 of each outer skirt contacting the upper edge 32 of an adjacent outer skirt (except at the inflow end of the frame) without any axial spacing between adjacent outer skirts. In other embodiments, the axial spacing between adjacent outer skirts can vary along the length of the frame. In addition, the height of the outer skirts (measured from the lower edge 30 to the upper edge 32) can vary from one skirt to the next.

The upper edges 32 of the outer skirts desirably are secured to the frame 12 and/or the inner skirt 16 at spaced-apart locations around the circumference of the frame to form a plurality of openings 38 that can received retrograde blood flow. In the illustrated embodiment, for example, the projections 34 of the outer skirts can be sutured to the struts 44 of the frame 12 and/or the inner skirt 16. As shown, the corners of the projections 34 of the first and second outer skirts 18, 20 can be folded over respective struts 44 and secured with sutures 52. The projections 34 of the third outer skirt 22 can be secured to the inner skirt 16 as shown or to the struts 44 at the outflow end 42 of the frame.

The notches 36 can remain unattached to the inner skirt 16 and the frame 12 to form the openings 38 during radial expansion of the prosthetic valve, as explained in further detail below. The outer skirts 18, 20, 22 may be attached to the inner skirt and/or frame such that the notches 36 and the openings 38 of the outer skirts 18, 20, 22 are aligned along the length of the valve (as shown in FIG. 1). Alternatively, the notches 36 and the openings 38 of one outer skirt can be angularly or circumferentially offset from the notches and the openings of another outer skirt. For example, the openings 38 of the first outer skirt 18 can be circumferentially offset from the openings 38 of one or both of second and third outer skirts 18, 20, 22 and the openings 38 of the second outer skirt 20 can be circumferentially offset from the openings 38 of one or both of the first and third outer skirts 18, 22.

Each of the outer skirts 18, 20, 22 may be secured to the frame 12 such that when the frame is in its expanded state, there is excess material or slack between the lower and upper edges 30, 32 of the skirt that does not lie flat against the outer surface of the frame 12. In other words, the outer skirts 18, 20, 22 can include excess material, which causes the skirts to billow outwardly as the frame foreshortens (i.e., shortens in length) during radial expansion.

When the valve 10 is deployed within the body (e.g., within the native aortic valve), the outer skirts 18, 20, 22 can cooperate with the inner skirt 16 to prevent or at least minimize paravalvular leakage. In another advantageous feature, the slack between the lower and upper edges of the two or more outer skirts allows the frame 12 to elongate axially during crimping without any resistance from the outer skirt.

The outer skirts 18, 20, 22 may lower the risk of paravalvular leakage (PVL) dramatically due to numerous mechanisms. PVL includes blood flowing through a channel between the structure of the implanted valve and cardiac tissue as a result of a lack of appropriate sealing between the prosthetic valve and the surrounding tissue. The disclosed valve may reduce PVL by means that are dynamic in nature (e.g. billowing of the skirt), and others may be based on elements that are meant to impede flow by means of turbulence. An example of how the disclosed prosthetic valve 10 may reduce PVL includes the physical obstruction to the flow. In other words, the outer skirts can extend into and fill gaps between the frame 12 and the surrounding native annulus to assist in forming a good fluid tight seal between the valve and the native annulus. Additionally and/or alternatively, due to the openings along the upper edges of the skirts, retrograde blood can flow into the openings and further open or radially expand the outer skirts with rising back pressure (e.g., diastolic pressure when implanted at the aortic position), similar to the action of a sail, to enhance the sealing of the skirts against the surrounding tissue.

Additionally and/or alternatively, in the long term, there may also be a biological cascade reaction that takes place that reduces PVL. In particular, fibrin deposition may initially seal the pores of the fabric material used for the outer skirts, which can lead to blood clotting, and in the long run, replacement of the outer skirts by fibrotic tissue.

Figure 6:
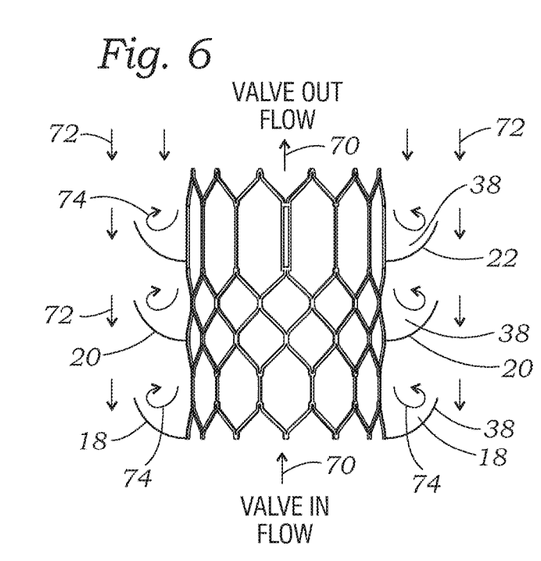
FIG. 6 is a schematic representation of the prosthetic heart valve of FIG. 1 showing the flow of blood on the outside of the prosthetic heart valve when implanted in a native heart valve annulus.

Additionally and/or alternatively, another mechanism by which the outer skirts can reduce PVL is turbulent flow created by the skirt openings 38. Explaining further, FIG. 6 shows the prosthetic valve 10 deployed within the body (e.g., the native aortic valve). Arrows 70 represent antegrade blood flow that flows through the prosthetic valve 10 (e.g., during systole for the aortic position) and arrows 72 represent retrograde blood flow that flows in the opposite direction on the outside of the prosthetic valve (e.g., diastole for the aortic position). Retrograde blood can flow into the openings 38, which create regions of turbulent blood flow at each of the outer skirts 18, 20, 22, as represented by arrows 74. The turbulent flow 74 interferes with the generally laminar retrograde flow 72, thereby reducing leakage or regurgitation through cavities larger than the outer diameter of the outer skirts. In other words, the multiple outer skirts can induce a series of turbulent flow obstructions along the leak path with each opening along the length of the prosthetic valve at least partially interrupting and reducing retrograde flow. Thus, when placed in series, the openings can produce sufficient turbulence along the length of the prosthetic valve to prevent or at least minimize PVL. In this manner, the sealing members may functionally operate in a manner similar to Tesla's Valvular Conduit. Moreover, multiple obstructions along the length of the prosthetic valve provided by the skirts can promote clotting and biologic sealing with the native tissue.

A prosthetic valve having multiple outer skirts placed in series can take advantage of the potentially high ratio between the length and diameter of the potential leak channel defined between the outside of the prosthetic valve and the surrounding adjacent anatomy. At higher ratios, a greater number of such obstructions can be implemented, thus creating a better seal. Moving in a direction from the inlet to the outlet of the prosthetic valve, the implantation zone for the prosthetic valve can start at the left ventricular outflow tract (LVOT) and end at the free edges of the native leaflets. The length of the potential leak channel can be maximized if the prosthetic valve extends along this entire interface. For example, the prosthetic valve can extend about 2-4 mm adjacent the LVOT and about 10-16 mm adjacent the aortic annulus and native leaflets. Thus, in this example, the anatomical sealing zone can be approximately 12-20 mm.

The number of skirts in the two or more skirts may be variable and may depend on valve design and on leak obstruction optimization. Additionally and/or alternatively, locations of the two or more skirts along the valve height as well as the height of each skirt may vary depending on the particular application.

Figure 7A:
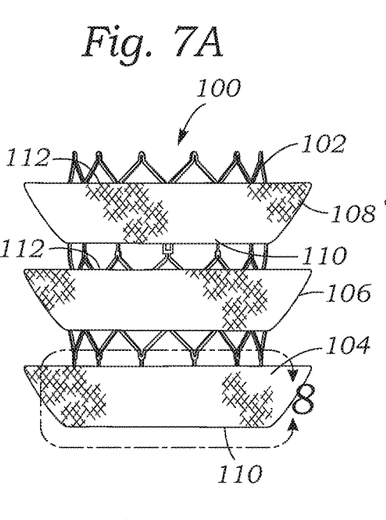
FIG. 7A is a side elevation view of a prosthetic valve having a plurality of outer skirts, according to another embodiment, in an expanded configuration.
Figure 7B:
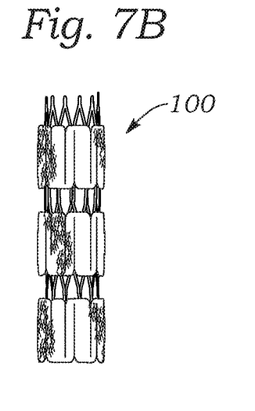
FIG. 7B is a side elevation view of the prosthetic valve of FIG. 7A in a collapsed configuration.
Figure 8:
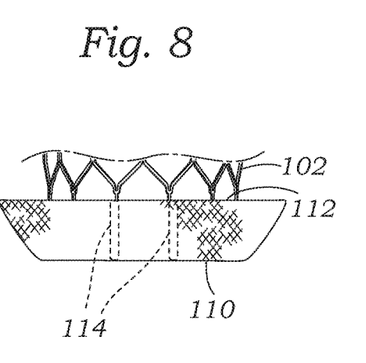
FIG. 8 is an enlarged view of the inflow end portion of the prosthetic valve of FIG. 7A.

FIGS. 7A, 7B and 8 show another embodiment of a prosthetic valve, indicated generally at 100. The prosthetic valve 100 can comprises a stent or frame 102, a plurality of outer skirts 104, 106, 108 positioned in series along the length of the frame, and a valvular structure (not shown in FIGS. 7 and 8 but can be the valvular structure 14). The prosthetic valve 100 can also include an inner skirt, such as the inner skirt 16. Each outer skirt can include a lower edge 110 secured to the outside of the frame 102 and an upper edge 112.

The outer skirts 104, 106, 108 differ from the outer skirts 18, 20, 22 in that the outer skirts 104, 106, 108 need not be connected to the frame 102 along their upper edges 112. As such, the entire upper edge 112 of each outer skirt can be radially spaced outwardly from the outer surface of the frame 102 when the prosthetic valve is deployed to form a continuous upper opening extending 360-degrees around the frame.

FIG. 7B shows the prosthetic valve 100 in a radially compressed state for delivery into a patient's body on a delivery catheter. In the delivery configuration, the outer skirts 104, 106, 108 can be folded against the outer surface of the frame 102. When deployed inside the body (e.g., after being released from the sheath of the delivery catheter), the stent 102 can radially expand and the outer skirts can pivot away from the outer surface of the frame, as depicted in FIG. 7A. The outer skirts, which can be formed from PET fabric or another suitable material, can be shape-set to pivot away from the frame when deployed from the sheath.

In lieu of or in addition to shape-setting the skirt material, the outer skirts can include a plurality of struts 114 that are pivotally connected to the frame at the lower edges 110 of the skirts (as shown in FIG. 8). The struts 114 can be formed from a shape-memory metal (e.g., Nitinol) that are configured to pivot outwardly from the frame to bias the skirts to their deployed state when the prosthetic valve is deployed from the sheath. Alternatively, the outer skirts can comprise a fabric weave that include relatively more rigid fibers or filaments or metal wires (e.g., Nitinol wires) extending in the axial direction (from the lower edges 110 to the upper edges 112) that bias the skirts to their deployed state.

In some embodiments, one or more of the outer skirts of the prosthetic valve may include multiple openings projecting from the frame of the prosthetic valve. The height and angle of each opening may be optimized to maximize flow obstruction. Additionally and/or alternatively, one or more of the outer skirts may include fringes at the upper edges of the skirt material to further perturb the leak flow. Additionally and/or alternatively, the roughness of the surfaces of the outer skirts (the inner surfaces and/or the outer surfaces) can be increased to promote flow perturbation of retrograde blood, thereby enhancing the sealing effect of the skirts. The surface roughness can be increased by forming the skirts from a fabric or textile comprising a pile (a cut pile or loop pile), similar to the weave of a towel or carpet.

The materials used to form the soft components of a prosthetic valve, such as the skirts and the leaflets of the valvular structure typically are not visible under fluoroscopy. Consequently, it may be difficult for the physician to confirm that the prosthetic valve is oriented in the right direction with the inflow end of the prosthetic valve positioned upstream of the outflow end of the prosthetic valve prior to deployment. This may be particularly problematic if the frame of the prosthetic valve has an axially symmetric shape (the frame is symmetric relative to a plane perpendicular to the frame length) so that it may be difficult to discern the orientation of the frame under fluoroscopy.

Figure 9:
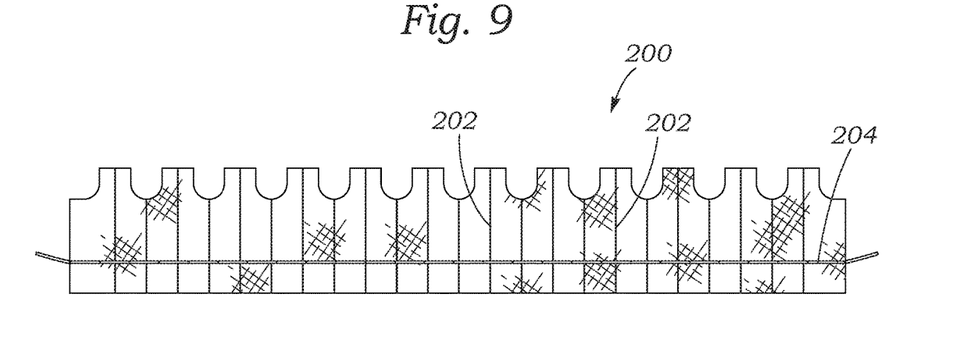
FIG. 9 shows another embodiment of a skirt laid out flat.

In particular embodiments, a prosthetic valve can have a skirt (which can be an outer skirt or an inner skirt) that has radiopaque markings to assist with proper orientation relative to the desired implantation site. FIG. 9 shows a skirt 200 having radiopaque markings in the form of, for example, vertical and/or horizontal lines 202, 204, respectively. The radiopaque markings on the skirt can also comprise various other shapes, such as diagonal lines, arrows, circles, etc.

The lines 202, 204 may be printed on the skirt fabric using a radiopaque dye. Additionally and/or alternatively, the lines 202, 204 may be formed on the skirt fabric using radiopaque sutures or threads. Both the dye and/or the sutures may include one or more radiopaque materials, such as platinum, platinum-iridium, gold and/or other metals. The radiopaque sutures can comprise, for example, conventional sutures (e.g., 6/0 sutures) coated with a radiopaque material or having radiopaque markings along the length of the sutures. Because the markings are visible under fluoroscopy, the physician can use the markings to confirm the prosthetic valve is mounted in the correct orientation on the delivery apparatus to prevent deployment of an inverted valve and to position the prosthetic valve relative to the desired implantation site.

Figure 10:
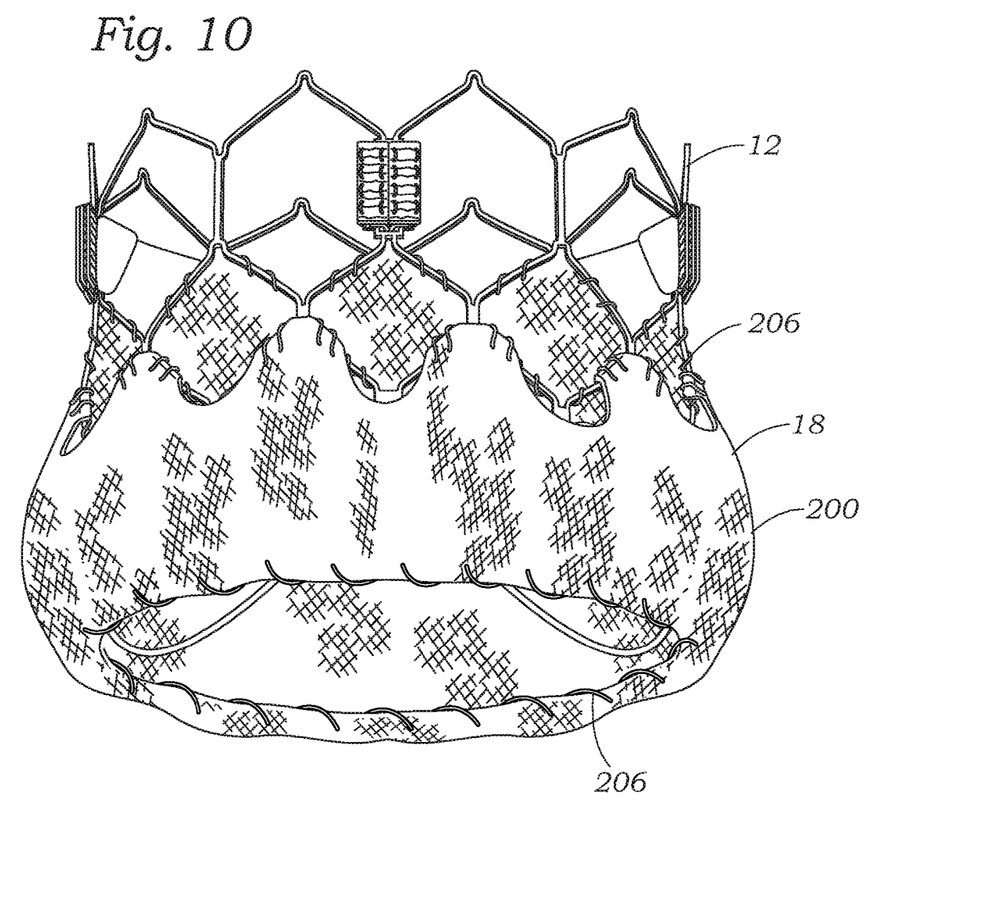
FIG. 10 shows the skirt of FIG. 9 secured to the frame of FIG. 3.

FIG. 10 shows a prosthetic valve similar to that shown in FIG. 1 but with the skirt 200 mounted to the outside of the frame. In lieu of or in addition to the radiopaque markings on the skirt 200, radiopaque sutures 206 can be used to secure the lower and/or upper edge of the skirt to the frame 12. The radiopaque sutures 206 can be used to confirm the correct orientation of prosthetic valve and to facilitate proper axial positioning of the skirt within a calcified annulus during valve deployment. Additionally and/or alternatively, radiopaque sutures can be wrapped directly around or otherwise secured to selected struts of the frame, for example, the struts at the inflow and/or outflow ends of the frame or at the lower and/or upper edges of the skirt.

In view of the many possible embodiments to which the principles of the disclosed technology may be applied, it should be recognized that the illustrated embodiments are only preferred examples of the disclosure and should not be taken as limiting the scope of the disclosure. Rather, the scope of the disclosure is defined by the following claims. We therefore claim as our disclosure all that comes within the scope and spirit of these claims.

We claim:

1. An implantable prosthetic valve comprising:
an annular frame;
a leaflet structure positioned within the frame; and two or more annular outer skirts positioned around an outer surface of the frame, the two or more outer skirts each comprising an inflow edge secured to the frame and an outflow edge, wherein the outflow edges of the two or more outer skirts define one or more upper openings allowing retrograde blood to flow between the outer surface of the frame and the two or more skirts to create a plurality of regions of turbulent blood flow along the outside of the prosthetic valve; and wherein one or more of the outer skirts comprise a fabric formed with fringes that perturb the flow of blood along the outside of the prosthetic valve.

2. The valve of claim 1, wherein the inflow edge of at least one of the two or more outer skirts is secured to the frame with sutures including radiopaque material.

3. The valve of claim 1, wherein at least one of the two or more outer skirts comprises markings formed from radiopaque dye.

4. The valve of claim 1, wherein the outflow edges of at least two of the two or more outer skirts are secured at intervals to the frame and include openings between the intervals that are unsecured to the frame.

5. The valve of claim 1, wherein the one or more openings do not lie flat against the outer surface of the frame in an expanded configuration.

6. The valve of claim 1, wherein outflow edge of at least one of the two or more outer skirts is unsecured to the frame.

7. The valve of claim 1, wherein the axial spacing between the two or more outer skirts is less than the axial height of a least one of the two or more outer skirts.

8. The valve of claim 1, wherein the two or more outer skirts are positioned in series along the length of the frame between an inflow edge of the frame and an outflow edge of the frame.

9. The valve of claim 1, wherein the inflow edge of at least one of the two or more outer skirt contacts the outflow edge of another one of the two or more outer skirts without any axial spacing between.

10. An implantable prosthetic valve that is radially collapsible to a collapsed configuration and radially expandable to an expanded configuration, the prosthetic valve comprising:

an annular frame;

a leaflet structure positioned within the frame;

a plurality of outer skirts positioned around an outer surface of the frame, each outer skirt extending continuously around the entire extent of a circumference of the frame, each outer skirt comprising an inflow edge secured to the frame and an outflow edge; and wherein the outflow edge of each outer skirt comprises alternating projections and notches, the projections being secured to the frame and the notches being unsecured to the frame such that each notch defines an opening.

11. The valve of claim 10, wherein the first outer skirt comprises markings formed from radiopaque dye.

12. The valve of claim 10, wherein the plurality of outer skirts further includes a third outer skirt, wherein in the expanded configuration the third outer skirt includes notches unsecured to the frame between the projections.

13. The valve of claim 10, wherein the openings of the first outer skirt and the second outer skirt are circumferentially aligned.

14. The valve of claim 10, wherein the openings do not lie flat against the outer surface of the frame in the expanded configuration.

15. The valve of claim 10, wherein the inflow edge of the second outer skirt contacts the outflow edge of the first outer skirt without any axial spacing between.

16. The valve of claim 10, wherein the plurality of outer skirts are positioned in series along the length of the frame between an inflow edge of the frame and an outflow edge of the frame.

17. The valve of claim 10, wherein the axial height of a least two of the plurality of skirts is the same.

18. The valve of claim 1, wherein the fringes are formed along the outflow edges of the one or more outer skirts.

19. The valve of claim 10, wherein the plurality of skirts includes a first outer skirt and a second outer skirt, and wherein the notches of the first outer skirt are circumferentially offset from the notches of the second outer skirt.

* * * * *